United States Patent [19]

Loftus

[11] Patent Number: 4,497,949
[45] Date of Patent: Feb. 5, 1985

[54] PROCESS FOR THE MANUFACTURE OF CEPHALOSPORIN DERIVATIVES

[75] Inventor: Frank Loftus, Macclesfield, England

[73] Assignee: Imperial Chemical Industries PLC, London, England

[21] Appl. No.: 388,167

[22] Filed: Jun. 14, 1982

[51] Int. Cl.$^3$ ................. C07D 501/36; A61K 31/425
[52] U.S. Cl. ........................ 544/27; 544/28; 544/22; 544/26
[58] Field of Search ............... 544/16, 22, 26, 27, 544/90, 28; 424/248.4, 246

[56] References Cited

U.S. PATENT DOCUMENTS 2,331,671 10/1943 Ericks ................................. 260/551
4,358,447 11/1982 Hannah ................................ 544/22

FOREIGN PATENT DOCUMENTS 31708 7/1981 European Pat. Off. .
1132013 10/1968 United Kingdom .

OTHER PUBLICATIONS

J. Chem. Soc., 1956, 307-310.
J. Amer. Chem. Soc., 1955, 77, 1056.

Primary Examiner—Nicholas S. Rizzo
Attorney, Agent, or Firm—Cushman, Darby & Cushman

[57] ABSTRACT

The invention relates to a process for the manufacture of a cephalosporin derivative of the formula I:

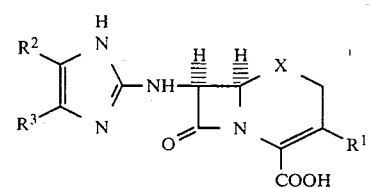

in which X is a sulphur or oxygen atom or a sulphinyl radical, $R^1$ is any one of the C-3 substituents from antibacterially-active cephalosporins known in the art, $R^2$ is a hydrogen atom or a 1-6C alkyl or 2-6C alkenyl radical, $R^3$ is a hydrogen atom or one of a variety of radicals defined in the specification, and the pharmaceutically-acceptable acid- and base-addition salts thereof, characterized by reaction of a compound of the formula IX:

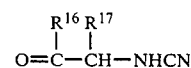

in which $R^{16}$ and $R^{17}$ individually have one of the values given above for $R^2$ and $R^3$, or a derivative thereof in which the carbonyl group is masked, with a compound of the formula X:

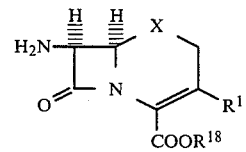

in which $R^{18}$ is a hydrogen atom or any one of the cephalosporin 3-carboxylic acid protecting groups known in the art; whereafter, when $R^{18}$ is other than a hydrogen atom, the protecting group $R^{18}$ is replaced by hydrogen by conventional means.

5 Claims, No Drawings

PROCESS FOR THE MANUFACTURE OF CEPHALOSPORIN DERIVATIVES

This invention relates to a process for the manufacture of cephalosporin derivatives which have antibacterial properties.

In European Patent Publication No. 31708 there are described cephalosproin derivatives which have an optionally-substituted imidazol-2-ylamino radical attached at the 7-position of the cephalosporin nucleus. In this publication, the preferred method of attaching the imidazole ring is via the reaction of a 7-aminocephalosporin derivative with an optionally-substituted 2-fluoroimidazole. However, the preparation of such 2-fluoroimidazoles is difficult and tedious. The preparation of 2-aminoimidazoles by reaction of cyanamide with an aminoacetal is described in *J. Chem. Soc.,* 1956, 307. A similar reaction using a β-aminoketone is described in UK Pat. No. 1,132,013. It has now been discovered that if a cyanamido-aldehyde or -ketone, or a masked derivative thereof, is reacted with a 7-aminocephalosporin derivative, the 7-(imidazol-2-yl)aminocephalosporin derivatives of European Patent Publication No. 31708 may be readily prepared.

According to the invention there is provided a process for the manufacture of a cephalosporin derivative of the formula I:

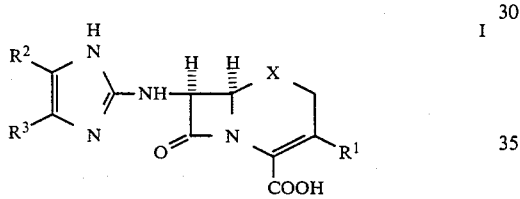

in which

X is a sulphur or oxygen atom or a sulphinyl radical;

$R^1$ is any one of the C-3 substituents from antibacterially-active cephalosporins known in the art;

$R^2$ is a hydrogen atom or a 1-6C alkyl or 2-6C alkenyl radical;

$R^3$ is a hydrogen atom or a 1-6C haloalkyl, 1-6C azidoalkyl, 2-6C cyanoalkyl, 2-6C carboxyalkyl, 3-8C alkoxycarbonylalkyl, 2-6C carbamoylalkyl, 3-8C alkylcarbamoylalkyl, 4-10C dialkylcarbamoylalkyl, 2-6C alkenyl, 2-6C nitroalkenyl, 8-15C arylalkenyl, 14-25C diarylalkenyl, 20-35C triarylalkenyl, 7-11C arylalkyl, 1-6C alkanoyl, 7-11C aroyl, carbamoyl, 2-6C alkylcarbamoyl, 3-8C dialkylcarbamoyl, 5-10C (dialkylaminoalkyl)carbamoyl, 7-11C arylcarbamoyl, thiocarbamoyl, 2-6C (alkyl)thiocarbamoyl, 3-8C (dialkyl)thiocarbamoyl, 7-11C (aryl)thiocarbamoyl, 5-10C (dialkylaminoalkyl)thiocarbamoyl, 2-6C alkoxyalkyl, 2-6C alkanoyloxyalkyl, 2-6C carbamoyloxyalkyl, 3-8C alkylcarbamoyloxyalkyl, 4-12C dialkylcarbamoyloxyalkyl, 2-6C alkanoylaminoalkyl, 3-8C haloalkanoylaminoalkyl, 8-15C aroylaminoalkyl, 2-6C ureidoalkyl, 3-8C (alkylureido)alkyl, 4-12C (dialkylureido)alkyl, 8-15C (arylureido)alkyl, 2-6C formylalkyl, 2-10C alkanesulphonylaminoalkyl or a 7-15C arenesulphonylaminoalkyl radical, a 2-6C alkyl substituted on different carbon atoms by two radicals selected from nitro, 2-8C dialkylamino, 7-15C (aryl) (alkyl)amino, 8-20C (arylalkyl) (alkyl)amino, 1-6C alkoxy, 1-6C alkylthio, 6-10C aryloxy, 6-10C arylthio, 7-11C arylalkoxy and 7-11C arylalkylthio radicals, a 2-6C alkyl radical substituted on one carbon atom by a nitro, 2-10C dialkylamino or 1-6C alkanoylamino radical and on a different carbon atom by a methyl radical which is itself substituted by two radicals selected from cyano, 2-6C alkoxycarbonyl and 1-6C alkanoyl radicals, a radical of the formula II, III, IV, V, VI, VII or VIII:

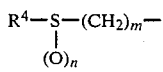

II

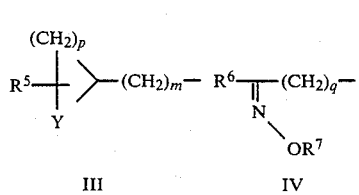

III                IV

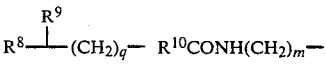

V                VI

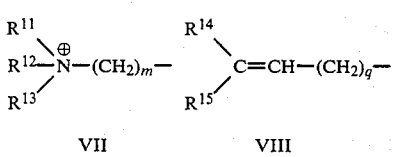

VII              VIII in which Y is an oxygen or sulphur atom or a $CH_2$ radical, m is 1 to 6, q is 0 to 6, n is 0 to 2, p is 1 to 4, $R^4$ is a 1-6C alkyl, 6-10C aryl or 7-11C aralkyl radical, $R^5$ is a hydrogen atom or a 1-6C alkyl or 6-10C aryl radical, $R^6$ is a hydrogen atom or a 1-6C alkyl, 6-10C aryl, 7-11C arylalkyl or heterocyclyl radical, $R^7$ is a hydrogen atom or a 1-6C alkyl radical which is optionally substituted by a carboxy, 2-6C alkoxycarbonyl, carbamoyl or cyano radical, $R^8$ is a heterocyclyl radical, $R^9$ is a hydroxy or amino radical, $R^{10}$ is a pyridyl radical, $R^{11}$, $R^{12}$ and $R^{13}$, which may be the same or different, are hydrogen atoms or 1-6C alkyl or 6-10C aryl radicals and $R^{14}$ and $R^{15}$, which may be the same or different, are cyano, nitro, 2-6C alkoxycarbonyl, 7-11C aryloxycarbonyl, 1-6C alkanoyl or 7-11C aroyl radicals, a heterocyclic radical which is linked (to the imidazole ring) by a direct bond or by a methylene or thiomethylene ($SCH_2$) bridge, a 1-6C alkyl, cyano, hydroxy, carboxy, 2-6C alkoxycarbonyl, 3-15C dialkylaminoalkyl or 1-6C hydroxyalkyl radical, or a phenyl radical optionally substituted by 1 or 2 radicals selected from halogen atoms and nitro, hydroxy, carboxy, cyano, 1-6C alkyl and 2-6C alkoxycarbonyl radicals;

and the pharmaceutically-acceptable acid- and base-addition salts thereof.

characterised by reaction of a compound of the formula IX:

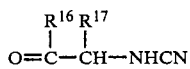

in which $R^{16}$ and $R^{17}$ individually have one of the values given above for $R^2$ and $R^3$, or a derivative thereof in which the carbonyl group is masked, with a compound of the formula X:

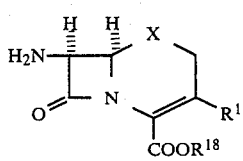

in which X and $R^1$ have the meanings stated above and $R^{18}$ is a hydrogen atom or any one of the cephalosporin 3-carboxylic acid protecting groups known in the art; whereafter when $R^{18}$ is other than a hydrogen atom the protecting group $R^{18}$ is replaced by hydrogen by conventional means;
and whereafter when the compound of the formula I is obtained in the form of the free base or a salt, and a pharmaceutically-acceptable salt or the free base respectively is required, any necessary conversion between free base and salt is carried out by conventional means.

It is to be understood that in the above formula I and throughout this specification the illustrated stereochemistry of the cephem nucleus of the formula XI:

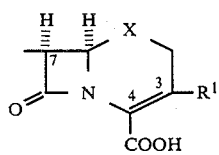

is the absolute configuration. It is also to be understood that when X is a sulphinyl radical the oxygen atom may be in the α or β configuration, or a mixture of these two. It is further to be understood that although the double bonds in the imidazole ring have been inserted in particular positions, other tautomeric forms are, in certain instances, possible and these tautomeric forms are included within the scope of this invention. Note however that the delta-3 double bond in the cephalosporin nucleus is fixed in position. When the compound of the formula I is present as the free base, it will generally exist in the form of the zwitterion.

A particular value for $R^1$ is a hydrogen or halogen atom (e.g. a fluorine, chlorine or bromine atom), a hydroxy or amino radical or a saturated or unsaturated, substituted or unsubstituted 1–20C organic group. Illustrative values for $R^1$ when it is a 1–20C organic group are as follows:

(a) 1–6C alkyl, benzyl optionally substituted by fluorine or methoxy, 1–6C haloalkyl, formyl, carboxy, 1–6C alkoxy, 1–6C alkylthio, 1–6C alkylamino, phenylamino, benzylamino, 3–6C cycloalkylamino, cyano, 2–6C alkoxycarbonyl, 2–6C alkanoyl, 3–10C alkoxycarbonylalkyl, 2–6C alkoxycarbonylamino, 2–6C alkylthiocarbonylamino, piperidino, pyrrolidino, morpholino, 2–6C alkanoylamino, ureido, 2–6C alkylureido, 3–8C dialkylureido, 1–6C alkanesulphinyl, 1–6C alkanesulphonyl, heterocyclyl and heterocyclylthio radicals in which the heterocycle is a 1,3,4-thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl radical optionally substituted in the 1- or 5-position, the optional substituents in each of these heterocycles being a 1–6C alkyl, a 1–6C sulphoalkyl, a 2–6C carboxyalkyl, a 1–6C haloalkyl or a 3–6C alkylthioalkyl radical or a pyridazin-3-yl, oxazol-3-yl or thiazol-3-yl each optionally substituted by 1 or 2 radicals selected from 1–6C alkyl, 1–6C haloalkyl and 2–6C alkoxycarbonyl radicals;

(b) radicals of the formula XII:

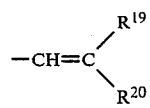

in which $R^{19}$ and $R^{20}$, which may be the same or different, are hydrogen atoms, 1–6C alkyl, 5–7C cycloaliphatic, 6–12C aryl, 7–10C arylalkyl, (e.g. benzyl, 2-phenylethyl), formyl, cyano, carboxy, 2–6C alkoxycarbonyl, sulpho, 1–6C alkanesulphinyl, 1–6C alkanesulphonyl, 1–6C alkoxy, 1–6C alkylthio, carbamoyl, nitro, 1–6C hydroxyalkyl, methylcarbamoyloxymethyl, benzylcarbamoyloxymethyl, 2–6C alkoxymethyl, 2–6C alkylthiomethyl, 2-haloethoxymethyl, cyclopentyloxymethyl, benzyloxymethyl or 3–8C alkanoyloxymethyl radicals or radicals of the formula $CH_2SHet^1$ in which $Het^1$ is a 1,3,4-thiadiazol-2-yl or 1,3,4-oxadiazol-2-yl, both optionally substituted in the 5-position by a methyl radical, a 1H-triazol-5-yl radical optionally substituted in the 1-position by a methyl radical or a 1H-1,2,3-triazol-4-yl radical;

(c) radicals of the formula XIII:

in which $R^{21}$ is a cyano, carboxy or 2–6C alkoxycarbonyl radical;

(d) radicals of the formula XIV:

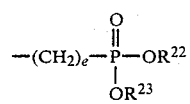

in which $R^{22}$ and $R^{23}$, which may be the same or different, are hydrogen atoms or 1–6C alkyl radicals and e is 1 to 4;

(e) radicals of the formula $CH_2Y$ in which Y is an atom or group which is the residue of a nucleophile or a derivative of a residue or a nucleophile, such a nucleophile or a derivative thereof being:

A. 3–15C trialkylamines;
B. heterocyclic amines having more than one heteroatom, at least one heteroatom being nitrogen;
C. pyridines which are optionally substituted by 1 to 3 substituents selected from halogen atoms and 1–6C alkyl, 6–10C aryl, 7–11C arylalkyl, 2–10C alkoxyalkyl, 3–10C alkanoyloxymethyl, formyl, carbamoyl, 2–6C alkanoyloxy, 2–6C alkoxycarbonyl, 1–6C alkoxy, 6–10C aryloxy, 7–11C aralkoxy, 1–6C alkylthio, 6–10C arylthio, 7–11C aralkylthio, cyano, hydroxy, 2–6C alkylcarbamoyl, 3–10C dialkylcarbamoyl, 2–6C (hydroxyalkyl)carbamoyl and 2-6C carbamoylalkyl radicals;
D. azide radicals;
E. amino, 1-6C alkanoylamino and 7-11C aroylamino radicals;
F. cyanide, pyrroles and substituted pyrroles;
G. nucleophiles giving rise to $R^1$ of the formula XV:

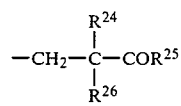

$$-CH_2-\underset{R^{26}}{\overset{R^{24}}{\underset{|}{\overset{|}{C}}}}-COR^{25} \qquad XV$$

in which $R^{24}$ and $R^{25}$, which may be the same or different, are selected from hydrogen atoms and cyano, 1-6C alkyl, 2-6C alkoxycarbonyl, 8-20C mono- or di-arylalkoxycarbonyl, 2-6C alkanoyl, 7-11C aralkyl, cyclopentyl and cyclohexyl radicals, and phenyl radicals optionally substituted by 1 or 2 radicals selected from halogen atoms and 1-6C alkyl, 1-6C alkoxy, 1-6C alkylamino, nitro and amino radicals, and $R^{26}$ is selected from hydrogen, 1-6C alkyl, 7-11C aralkyl, cyclopentyl and cyclohexyl radicals, and phenyl radicals optionally substituted or 1 or 2 radicals selected from halogen atoms, 1-6C alkyl, 1-6C alkoxy and 1-6C alkylamino radicals;
H. thiourea optionally substituted by a 1-6C alkyl, 6-10C aryl, 5-7C alicyclic or a heterocyclic radical, dithiocarbamates, thioamides substituted by a 1-6C alkyl or 6-10C aryl radical or thiosemicarbazides, thiosulphates, arylthioacids or heterocyclicthioacids of up to 10 carbon atoms and dithioacids of the formula XVI:

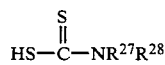

$$HS-\overset{S}{\overset{\|}{C}}-NR^{27}R^{28} \qquad XVI$$

in which $R^{27}$ and $R^{28}$, which may be the same or different, are hydrogen atoms, 1-6C alkyl, 2-6C hydroxyalkyl, 3-8C alkylaminoalkyl, 4-10C dialkylaminoalkyl or phenyl radicals, or $R^{27}$ and $R^{28}$ are joined to form a pyrrolidine, piperidine or morpholine ring or a piperazine ring which is optionally substituted on the nitrogen atom by one or two (in quaternised form) radicals selected from 1-6C alkyl and 3-6C alkenyl radicals;
I. compounds of the formula $R^{29}S(O)_dH$ in which d is 0, 1 or 2 and $R^{29}$ is a 1-6C alkyl, 5-7C alicyclic, 6-10C aryl optionally substituted by a carboxy radical, or 7-11C arylalkyl radical or a 5- or 6-membered heterocyclic ring (partially or fully unsaturated) containing 1 to 4 nitrogen atoms which ring may further include (where possible) oxygen and/or sulphur atom, in which the nitrogen atom or atoms may be in the oxide form, which heterocyclic ring may be fused with another heterocyclic ring within the same definition or may be fused with a benzene ring, the above aryl, arylalkyl, heterocyclic or fused benzene ring being optionally substituted (where possible) by 1 or 2 substituents selected from halogen atoms and 1-6C alkyl, 1-6C haloalkyl, 6-10C aryl, 2-6C alkenyl, 1-6C alkoxy, oxo, hydroxy, mercapto, amino, carboxy, cyano, isothiocyanate, carbamoyl, sulphamoyl, 2-6C alkoxycarbonyl, 3-6C alkenyloxycarbonyl, 8-12C aralkylcarbonyl, 7-11C aryloxycarbonyl, 2-6C hydroxyalkyl, 3-6C dihydroxyalkyl, sulphoamino and 1-6C alkanesulphonylamino radicals and radicals of the formula $B-R^{30}$ in which B is a 2-8C straight or branched chain which may be interrupted by a sulphur or oxygen atom or by an NH or 1-6C N-alkyl radical and $R^{30}$ is a radical selected from hydroxy, mercapto, cyano, 1-6C alkylamino, 2-6C dialkylamino, 2-6C alkanoylamino, carboxy, sulpho, carbamoyl, sulphamoyl, amidino, guanidino, 2-6C alkoxycarbonyl, 2-6C alkylcarbamoyl, 2-6C dialkylcarbamoyl, 1-6C alkylsulphamoyl, 2-6C dialkylsulphamoyl, sulphoamino, ureido, 1-6C alkoxy, 1-6C alkylthio, 1-6C alkanesulphonyl, 2-6C alkanoyl and 2-6C alkanoyloxy radicals and radicals of the formula $-S-R^{31}$ in which $R^{31}$ is a 1-6C alkyl radical or a group of the formula $B-R^{30}$ in which B and $R^{30}$ have the meanings given above and radicals of the formula $NR^{32}R^{33}$ in which $R^{32}$ and $R^{33}$, which may be the same or different, are selected from 1-6C alkyl radicals, groups of the formula $B-R^{30}$ in which B and $R^{30}$ have the definitions given above, 1-6C alkoxycarbonyl, 2-6C alkanoyl, carbamoyl, 2-6C alkylcarbamoyl and 3-10C dialkylcarbamoyl radicals;
J. radicals of the formula $R^{34}-OH$ in which $R^{34}$ is a hydrogen atom or a 1-6C alkyl, 3-6C alkenyl, 3-6C alkynyl, 5-7C cycloalkyl, 6-12C cycloalkylalkyl, 6-10C aryl, 7-11C arylalkyl or furfuryl radical, any of which may be substituted by 1 or 2 radicals selected from halogen atoms, and 1-6C alkyl, nitro, hydroxy, carboxy, 2-6C alkanoyloxy, 2-6C alkoxycarbonyl, 2-6C alkanoyl, 1-6C alkanesulphonyl, 1-6C alkoxysulphonyl, amino, 1-6C alkylamino and 2-6C alkanoylamino radicals or $R^{34}$ is a carbamoyl radical;
K. radicals of the formula $R^{35}-Q-COOH$ in which Q is a direct bond, an oxygen or sulphur atom or an NH radical and $R^{35}$ is:
  (i) a hydrogen atom or a 1-6C alkyl radical which may be interrupted by an oxygen or sulphur atom or by an NH group or substituted by a cyano, carboxy, methoxycarbonyl, ethoxycarbonyl, hydroxy, carboxycarbonyl, or amino radical, or halogen atom;
  (ii) a 2-6C alkenyl radical which may be interrupted by an oxygen or sulphur atom or an NH group;
  (iii) a phenyl, hydroxyphenyl, chlorophenyl, fluorophenyl, tolyl, nitrophenyl, aminophenyl, methoxyphenyl, methylthiophenyl, thienyl, pyridyl, cyclohexyl, cyclopentyl, sydnonyl, naphthyl or ethoxynaphthyl radical; or
  (iv) $R^{36}-(CH_2)_g$ where $R^{36}$ has the value for $R^{35}$ listed in (i) above and g is 1 to 4;
and
(f) radicals of the formula XVII:

$$-CH=CH-S-R^{27} \qquad XVII$$

in which $R^{37}$ is
(1) a 1-6C alkyl (e.g. methyl), L-2-amino-2-carboxyethyl or phenyl radical;
(2) a pyridyl radical or the N-oxide thereof;
(3) a pyridazin-3-yl radical substituted in the 6-position by a 1-6C alkyl (e.g. methyl), methoxy, amino or 1-6C acylamino (e.g. acetylamino) radical, or the N-oxide thereof, or a pyrimidin-2-yl or tetrazolo[4,5-b]pyridazin-6-yl radical;
(4) a 5,6-dioxo-1,4,5,6-tetrahydro-1,2,4-triazin-3-yl radical substituted in the 4-position; 1,3,4-triazol-5-yl or 2-alkoxycarbonyl-1,3,4-triazol-5-yl radical in which the alkoxycarbonyl is 2-6C (e.g. methoxycarbonyl), each substituted in the 1-position:
(a) by a 1-6C alkyl (e.g. methyl) radical optionally substituted by a 1-6C alkoxy (e.g. methoxy), 1-6C alkylthio (e.g. methylthio), phenyl, formyl, carbamoyl, 2-6C alkylcarbamoyl (e.g. methylcarbamoyl), 3-10C dialkylcarbamoyl (e.g. dimethylcarbamoyl), 1-6C alkanoyl (e.g. acetyl), 2-6C alkoxycarbonyl (e.g. methoxycarbonyl) or thiazolidin-2-yl radical;
(b) by an allyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxyprop-2-yl radical;
(c) by a 2-4C alkyl radical which is substituted by a hydroxy, carbamoyloxy, 1-6C alkanoyl (e.g. acetyl) (which can itself be optionally substituted by an amino, 1-6C alkylamino [e.g. methylamino] or 2-10C dialkylamino [e.g. dimethylamino] radical), 1-6C alkanesulphinyl (e.g. methanesulphinyl), 1-6C alkanesulphonyl (e.g. methanesulphonyl), amino, 1-6C alkylamino (e.g. methylamino), 2-10C dialkylamino (e.g. dimethylamino), sulphoamino, 1-6C alkanesulphonylamino (e.g. methanesulphonylamino), sulphamoylamino, 1-6C alkanoylamino (e.g. acetylamino) (which can itself be optionally substituted by a hydroxy, amino, 1-6C alkylamino [e.g. methylamino] 2-10C dialkylamino [e.g. dimethylamino] radical), 2-6C alkoxycarbonylamino (e.g. methoxycarbonylamino), ureido, 2-6C alkylureido (e.g. methylureido) or 3-10C dialkylureido (e.g. dimethylureido) radical;
(d) by a radical of the formula XVIII, XIX or XX:

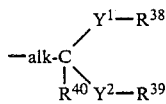

XVIII

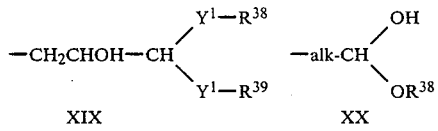

XIX        XX in which alk is a 1-4C alkylene (e.g. ethylene) radical, $Y^1$ and $Y^2$ are the same and are oxygen or sulphur atoms and $R^{38}$ and $R^{39}$ are the same and are 1-6C alkyl (e.g. methyl) radicals or $Y^1$ and $Y^2$ are the same or different and are oxygen or sulphur atoms and $R^{38}$ and $R^{39}$ are joined to form a 2-3C alkylene radical, and $R^{40}$ is a hydrogen atom or a 1-3C alkyl (e.g. methyl) radical;
(e) by a 1-6C alkyl (e.g. methyl) radical substituted by a 1-6C alkoxyimino (e.g. methoxyimino) or hydroxyimino radical;
(5) a 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl radical in each of which the alkyl is 1-6C (e.g. methyl);
(6) a 1,3,4-triazol-5-yl, 1,2,3-triazol-5-yl or 1-alkyl-1,2,4-triazol-5-yl radical in which the alkyl is 1-6C (e.g. methyl) which is optionally substituted in the 3-position by a 2-6C alkoxycarbonyl (e.g. methoxycarbonyl) radical;
(7)a. a 1,3,4-thiadiazol-5-yl radical optionally substituted by a 1-6C alkyl (e.g. methyl), trifluoromethyl, 1-6C alkoxy (e.g. methoxy), 1-6C alkylthio (e.g. methylthio), 2-4C hydroxyalkylthio (e.g. 2-hydroxyethylthio), 1-6C alkanesulphonyl (e.g. methanesulphonyl), hydroxy, 1-6C hydroxyalkyl (e.g. hydroxymethyl), carboxy, 2-6C carboxyalkyl (e.g. carboxymethyl), amino, 1-6C alkylamino (e.g. methylamino), 2-10C dialkylamino (e.g. dimethylamino), 1-6C aminoalkyl (e.g. 2-aminoethyl), 2-8C alkylaminoalkyl (e.g. 2-methylaminoethyl), 3-12C dialkylaminoalkyl (e.g. 2-dimethylaminoethyl), 1-6C alkanoylamino (e.g. acetylamino) or 2-8C alkanoylaminoalkyl (e.g. acetylaminoethyl) radical, or
b. a 1,2,4-thiadiazol-5-yl radical substituted by a 1-6C alkyl (e.g. methyl) or 1-6C alkoxy (e.g. methyl) radical;
(8)a. a 1,3,4-oxadiazol-5-yl radical which is optionally substituted by a 1-6C alkyl (e.g. methyl), trifluoromethyl, phenyl, 1-6C aminoalkyl (e.g. aminomethyl), 2-8C alkylaminoalkyl (e.g. methylaminomethyl), 3-10C dialkylaminoalkyl (e.g. 2-dimethylaminoethyl) or 2-8C alkanoylaminoalkyl (e.g. acetylaminomethyl) radical or
b. an oxazol-2-yl radical optionally substituted in the 4-position by a 1-6C alkyl (e.g. methyl) radical;
(9) a tetrazol-5-yl radical optionally substituted in the 1-position by:
(a) a 1-6C alkyl (e.g. methyl) radical itself optionally substituted by a 1-6C alkoxy (e.g. methoxy), sulpho, carboxy, formyl or sulphamoyl radical;
(b) a 2-4C alkyl (e.g. ethyl) radical substituted by a hydroxy, amino, 1-6C alkylamino (e.g. methylamino), 2-8C dialkylamino (e.g. dimethylamino), 1-6C alkanoylamino (e.g. acetylamino), 2-6C carboxyalkylamino (e.g. carboxymethylamino), sulphamoylamino, sulphoamino, ureido, 2-6C alkylureido (e.g. methylureido) or 3-8C dialkylureido (e.g. dimethylureido) radical;
(c) a 1-5C alkyl (e.g. ethyl) radical substituted by a hydroxyimino or 1-6C alkoxyimino (e.g. methoxyimino) radical;
(d) a phenyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxy-2-propyl radical; or
(e) a radical of the formula XVIII above in which $R^{40}$ is a hydrogen atom, or a radical of the formula XIX above, in both of which $Y^1$, $Y^2$, $R^{38}$ and $R^{39}$ are as given above.

A particular value for $R^2$ is a hydrogen atom or a methyl or allyl radical.

A particular value for $R^3$ is a fluoromethyl, chloromethyl, bromomethyl, difluoromethyl, trifluoromethyl, azidomethyl, 3-azidopropyl, cyanomethyl, 2-cyanoethyl, carboxymethyl, 2-carboxyethyl, methoxycarbonylmethyl, carbamoylmethyl, 2-carbamoylethyl, methylcarbamoylmethyl, dimethylcarbamoylmethyl, vinyl, allyl, 2-nitrovinyl, 2-phenylvinyl, 1-phenylvinyl, 2-phenylallyl, 3-phenylallyl, 1,2-diphenylvinyl, 2,2-diphenylvinyl, 2,3-diphenylallyl, 3,3-diphenylallyl, 1,2,2-triphenylvinyl, 2,3,3-triphenylallyl, benzyl, formyl, acetyl, benzoyl, carbamoyl, methylcarbamoyl, dimethylcarbamoyl, 2-dimethylaminoethylcarbamoyl, 3-dimethylaminopropylcarbamoyl, phenylcarbamoyl, thiocarbamoyl, (methyl)thiocarbamoyl, (dimethyl)thiocarbamoyl, (phenyl)thiocarbamoyl, (2-dimethylaminoethyl)thiocarbamoyl, methoxymethyl, 3-methoxpropyl, acetoxymethyl, 3-acetoxypropyl, carbamoyloxymethyl, methylcarbamoyloxymethyl, 3-(methylcarbamoyloxy)propyl, dimethylcarbamoyloxymethyl, acetylaminomethyl, 2-acetylaminoethyl, 3-acetylaminopropyl, 2-trifluoroacetylaminoethyl, 3-trifluoroacetylaminopropyl, benzoylaminomethyl, ureidomethyl, 3-ureidopropyl, (3-methylureido)methyl, 2-(3-methylureido)ethyl, (3,3-dimethylureido)methyl, (3-phenylureido)methyl, formylmethyl, methanesulphonylaminomethyl, 2-(methanesulphonylamino)ethyl, 3-(methanesulphonylamino)propyl or benzenesulphonylaminomethyl radical, or an ethyl or propyl radical which is substituted on different carbon atoms by two radicals selected from nitro, dimethylamino, (phenyl)(methyl)amino, (benzyl)(methyl)amino, methoxy, methylthio, phenoxy, phenylthio, benzyloxy and benzylthio radicals, or an ethyl or propyl radical which is substituted on one carbon atom by a nitro, dimethylamino or acetylamino radical and on a different carbon atom by a methyl radical which is itself substituted by two radicals selected from cyano, methoxycarbonyl and acetyl radicals, or a radical of the formula II, III, IV, V, VI, VII or VIII given above in which Y is an oxygen or sulphur atom or a $CH_2$ radical, m is 1, 2, or 3, q is 0, 1 or 2, n is 0, 1 or 2, p is 1 to 4, $R^4$ is a methyl, ethyl, phenyl or benzyl radical, $R^5$ is a hydrogen atom or a methyl or phenyl radical, $R^6$ is a hydrogen atom or a methyl, phenyl, benzyl or heterocyclyl radical, $R^7$ is a hydrogen atom or a methyl or n-propyl radical optionally substituted by a carboxy, methoxycarbonyl, carbamoyl or cyano radical, $R^8$ is a heterocyclyl radical, $R^9$ is a hydroxy or amino radical, $R^{10}$ is a pyridyl radical, $R^{11}$, $R^{12}$ and $R^{13}$, which may be the same or different, are hydrogen atoms or methyl or phenyl radicals, and $R^{14}$ and $R^{15}$, which may be the same or different, are cyano, nitro, methoxycarbonyl, phenoxycarbonyl, acetyl or benzoyl radicals, or $R^3$ is a heterocyclic radical which is linked (to the imidazole ring) by a direct bond or by a methylene or thiomethylene ($SCH_2$) bridge, or $R^3$ is a methyl, cyano, hydroxy, carboxy, methoxycarbonyl, dimethylaminomethyl, hydroxymethyl, 2-hydroxyethyl or pyridyl radical of a phenyl radical optionally substituted by
  1 or 2 radicals selected from fluorine, chlorine and bromine atoms and nitro, hydroxy, carboxy, cyano, methyl and methoxycarbonyl radicals.

A preferred group of compounds which may be prepared by the process of the invention are those of the formula I in which X is a sulphur atom, $R^2$ and $R^3$ are hydrogen atoms and $R^1$ is a hydrogen or chlorine atom or a methyl, acetoxymethyl, methoxymethyl, hydroxymethyl, azidomethyl, aminomethyl, benzoyloxymethyl, acetylaminomethyl, carbamoyloxymethyl or 2-(1-methyltetrazol-5-ylthio)trans-vinyl radical or a radical of the formula $CH_2S(O)_d$—$R^{29}$ in which d and $R^{29}$ have the meanings given above. In particular $CH_2S(O)_d$—$R^{29}$ may represent a 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-d]pyrimidin-2-ylthiomethyl radical.

A particularly preferred compound which may be manufactured by the process of the invention is that of the formula I in which X is a sulphur atom, $R^2$ and $R^3$ are hydrogen atoms and $R^1$ is a 1H-1,2,3-triazol-4-ylthiomethyl radical A particular value for $R^{18}$ when it is other than a hydrogen atom is a t-butyl or diphenylmethyl radical (replaceable by hydrogen using an acid such as formic or trifluoroacetic acid), a benzyl or substituted benzyl radical, for example a p-nitrobenzyl or p-methoxybenzyl radical (replaceable by hydrogen by hydrogenolysis) or a 2,2,2-trichloroethyl radical (replaceable by hydrogen using zinc/acetic acid). Alternatively $R^{18}$ may be a more labile protecting group which is replaced by hydrogen during the course of the reactions, thus avoiding the need for a separate deprotection process. Examples of such more labile protecting groups are those radicals which are used in the art to act as biological precursors for the 4-carboxy radical in cephalosporins. A particular value for such a labile protecting group is one of the formula XXI, XXII, XXIII, XXIV, XXV, XXVI, XXVII, XXVIII, XXIX, XXX, XXXI or XXXII:

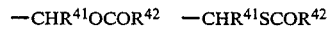

XXI  XXII

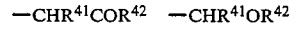

XXIII  XXIV

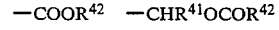

XXV  XXVI

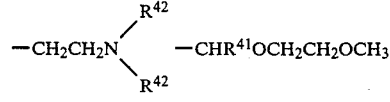

XXVII  XXVIII

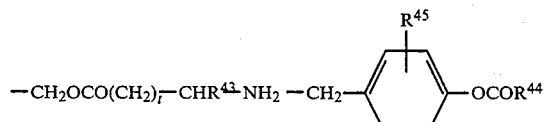

XXIX  XXX

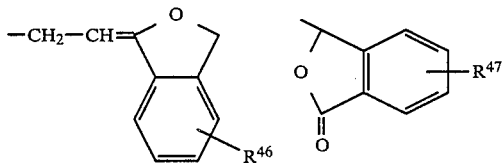

XXXI    XXXII in which $R^{41}$ is a hydrogen atom or 1-6C alkyl radical, $R^{42}$ is a 1-6C alkyl radical, $R^{43}$ is a hydrogen atom, or a 1-6C alkyl, 7-11C arylalkyl or 2-6C alkoxycarbonyl radical, t is 0 or 1, $R^{44}$ is a 1-6C alkyl, 6-10C aryl or a 7-11C aralkyl radical, $R^{45}$ is a hydrogen atom or one, two or three radicals selected from halogen atoms and nitro, cyano, 1-6C alkyl, 1-6C alkoxy, 1-6C alkylthio, 1-6C alkylsulphinyl, 1-6C alkanesulphonyl, 2-6C alkoxycarbonyl, 2-6C alkoxythiocarbonyl, 2-6C alkanoylamino, 6-10C aryl, 6-10C aryloxy, 6-10C arylthio, 6-10C arylsulphinyl, 6-10C arylsulphonyl, 7-11C aryloxycarbonyl, 7-11C arylthio carbonyl, and 7-11C aryloxythiocarbonyl radicals, $R^{46}$ is a hydrogen atom or one of the values for $R^{44}$ given above and $R^{47}$ is a hydrogen atom or one, two or three radicals selected from halogen atoms and 1-6C alkyl and 1-6C alkoxy radicals.

A particular masked derivative of the compound of the formula IX is one of the formula XXXIII:

in which $R^{16}$ and $R^{17}$ have the values given above, A and B are oxygen or sulphur atoms or sulphinyl or NH radicals and $R^{48}$ and $R^{49}$ are joined to form an ethylene or propylene chain which is optionally substituted by one or two 1-6C alkyl (e.g. methyl) radicals, or when A and B are oxygen or sulphur atoms or sulphinyl radicals, $R^{48}$ and $R^{49}$, which may be the same or different, are 1-6C alkyl or 1-6C alkanoyl radicals, or when A and B are both oxygen atoms and $R^{16}$ is a hydrogen atom, $R^{48}$ and $R^{49}$ are joined to form a 1,3,5-trioxane ring which is substituted on the remaining two carbon atoms by radicals of the formula XXXIV:

in which $R^{17}$ has the value given above.

A particular value for $R^{48}$ and $R^{49}$ when they are alkyl or alkanoyl radicals are methyl, ethyl, isopropyl, butyl, isobutyl or acetyl radicals.

A preferred value for A and B is an oxygen atom. A preferred value for $R^{41}$ and $R^{42}$ is that they both be the same and are methyl, ethyl, isopropyl, butyl or isobutyl radicals.

The process of the invention may be carried out in a diluent or solvent such as water, a 3-8C alkylketone (for example acetone) or 1,2-dimethoxyethane, a mixture of any two of these, or a mixture of any one or two of these with a 1-6C alkanol (for example methanol or ethanol), dimethylformamide, dimethylsulphoxide, sulpholane, tetrahydrofuran or other water-soluble ether such as dioxan. A preferred diluent or solvent is a mixture of water and 1,2-dimethoxyethane.

The process of the invention is preferably catalysed by an acid such as a mineral acid (for example sulphuric, hydrochloric, hydrobromic or nitric acid) or an organic acid such as a sulphonic acid (for example methanesulphonic, ethanesulphonic or toluene-p-sulphonic acid) or a carboxylic acid (for example formic, acetic, propionic or trifluoroacetic acid). A preferred acid is toluene-p-sulphonic, sulphuric or hydrochloric acid.

A suitable pH for the process of the invention is in the range 1 to 4, and the preferred range is 1.5 to 3.

A suitable temperature for carrying out the process of the invention is in the range 0° C. to the boiling point of the diluent or solvent, more particularly 20° to 100° C. A preferred range is ambient temperature to 70° C. and a particularly preferred range is 50° to 70° C.

The process of the invention may be conducted over a time period of from 10 seconds to several days, the preferred time period being from 3 minutes to 8 hours.

The reactants of the formulae II and III may be used in equimolar amounts, but it is advantageous if the reactant of the formula II is present in excess, preferably using about three molecular equivalents.

When $R^{18}$ is other than a hydrogen atom, its replacement by a hydrogen atom may be carried out in situ without isolation of the intermediate. Alternatively, the intermediate may be isolated and the deprotection carried out separately.

The compound of the formula IX and the derivatives thereof in which the carbonyl group is masked are novel and these compounds are therefore provided as a further feature of the invention.

The compound of the formula IX in which the carbonyl group is masked may be prepared by reaction of the corresponding amine with cyanogen bromide or cyanogen chloride, for example as illustrated in Examples 1 and 8. The amide intermediate may be prepared by standard methods. Thus, for example, the starting material of the formula IX in which $R^{17}$ has certain of the values given above for $R^3$ may be prepared by reaction of a compound of the formula XXXV:

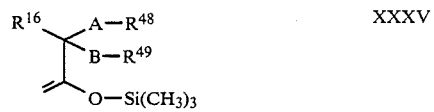

with an electrophilic reagent followed by transformation of the resulting carbonyl derivative to the corresponding amine. Alternatively, the compound of the formula IX in which the carbonyl group is masked may be prepared by reaction of a compound of the formula XXXVI:

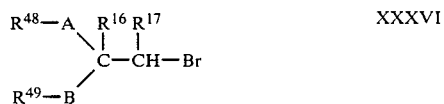

with cyanamide.

The process is illustrated but not limited by the following Examples. In particular the yields quoted are to be regarded as illustrative rather than limiting. Examples 1 and 8 describe the preparation of the starting material of the formula II. The n.m.r. spectra are quoted in delta relative to tetramethylsilane (delta=0) as internal standard (s=singlet, d=doublet, t=triplet, q=quartet, m=multiplet, br=broad).

EXAMPLE 1

A solution of cyanogen bromide (2.12 g., 0.02 moles) in ether (20 ml.) was added dropwise over 35 minutes to a stirred ice-cooled solution of aminoacetaldehyde diethyl acetal (5.32 g., 0.04 moles) in ether (20 ml.). During this addition a white precipitate was formed. The resulting suspension was stirred at 0° C. for a further hour, filtered and the filtrate evaporated to dryness under reduced pressure to give 2,2-diethoxyethylcyanamide (3.47 g., 110%) as a colourless oily liquid having the following n.m.r. spectrum in CDCl$_3$: 1.24 (t, 6H); 3.1 (d, 2H); 3.65 (m, 4H); 4.0 (br s, 1H); 4.57 (t, 1H).

EXAMPLE 2

A suspension of 7-amino-3-acetoxymethylceph-3-em-4-carboxylic acid (1.36 g., 5 m moles) in a solution of conc. sulphuric acid (0.27 ml., 5 m moles) in water (5 ml.) was heated rapidly to reflux and stirred while 2,2-diethoxyethylcyanamide (1.73 g., 10 m moles) was added dropwise over 1 minute. The resulting mixture was heated under reflux for a further minute and then cooled. Saturated aqueous sodium acetate (5 ml.) was added, followed by water (25 ml.). The resulting orange precipitate was removed by filtration and the filtrate evaporated to dryness. The residual gum was purified by high pressure liquid chromatography on a "Lichro-Prep" RP-18 ("LichroPrep" is a Trade Mark) column using methanol/water/acetic acid 20:80:1 v/v/v as eluant to give 0.1505 g. (9%) of 7-(imidazol-2-yl)amino-3-acetoxymethylceph-3-em-4-carboylic acid having the following n.m.r. spectrum in d$_6$ dimethylsulphoxide (d$_6$DMSO): 2.1 (s, 3H); 3.3–3.9 (m, 2H); 4.8 (d, 1H); 5.15 (d, 1H); 5.3 (d, 1H); 5.7 (d, 1H); 7.1 (s, 2H); 9.4 (d, 1H).

EXAMPLE 3

To a solution of t-butyl 7-amino-3-acetoxymethylceph-3-em-4-carboxylate (1.64 g., 5 m moles) in a mixture of acetone (15 ml.) and water (5 ml.) was added toluene-p-sulphonic acid monohydrate (0.95 g., 5 m moles) and the resulting solution was heated under reflux with stirring while a solution of 2,2-diethoxyethylcyanamide (1.73 g.,~10 m moles) in acetone (10 ml.) was added dropwise over 1.5 hours. After 4 hours at reflux temperature the reaction mixture was cooled and the solvent evaporated under reduced pressure. The residual gum was partitioned between ethyl acetate (50 ml.) and saturated aqueous sodium bicarbonate (25 ml.), the organic layer separated and extracted with cold 1N aqueous HCl (25 ml.). The acid layer was separated, washed with ethyl acetate, basified with excess sodium bicarbonate and extracted with ethyl acetate. The organic layer was washed with water (25 ml.). Water (25 ml.) was then added to the ethyl acetate layer, followed by conc. aqueous HCl till the pH of the aqueous layer was 3.5. The aqueous layer was separated, washed with ethyl acetate and basified with excess sodium bicarbonate. The mixture was extracted with ethyl acetate (25 ml., 10 ml.) and the combined extracts dried (MgSO$_4$) and the solvent evaporated under reduced pressure to give 0.33 g. (16.8%) of t-butyl 3-acetoxymethyl-7-(imidazol-2-yl)aminoceph-3-em-4-carboxylate having the following n.m.r. in CDCl$_3$+CD$_3$OD: 1.6 (s, 9H), 2.15 (s, 3H); 3.3 (d, 1H); 3.7 (d, 1H); 4.8 and 5.15 (2d, 2H); 5.25 (d, 1H); 5.7 (d, 1H); 6.8 (s, 2H).

A solution of this product in trifluoroacetic acid (1 ml.) was stirred at room temperature for 30 minutes. The solvent was evaporated under reduced pressure and the residue was triturated with ether to give 3-acetoxymethyl-7-(imidazol-2-yl)aminoceph-3-em-4-carboxylic acid having an n.m.r. spectrum identical to that of the product in Example 2.

EXAMPLE 4

To a solution of t-butyl 7-amino-3-acetoxymethylceph-3-em-4-carboxylate (15.78 g., 0.048 moles) in a mixture of water (48 ml.) and acetone (144 ml.) was added toluene-p-sulphonic acid monohydrate (9.12 g., 0.048 moles) and the resulting solution was heated under reflux with stirring while a solution of 2,2-diethoxyethylcyanamide (15.88 g., 0.096 moles) in acetone (96 ml.) was added dropwise over 1.75 hours. After 4 hours at reflux temperature further 2,2-diethoxyethylcyanamide (7.94 g., 0.048 moles) was added and the mixture heated under reflux for a further 3 hours. The reaction mixture was worked up as described in Example 3 to give 6.83 g. (36%) of t-butyl 3-acetoxymethyl-7-(imidazol-2-yl)aminoceph-3-em-4-carboxylate.

EXAMPLE 5

To a solution of diphenylmethyl 7-amino-3-(1H-1,2,3-triazol-4-yl)thiomethylceph-3-em-4-carboxylate (0.479 g., 1 m moles) in acetone (5 ml.) was added toluene-p-sulphonic acid monohydrate (0.19 g., 1 m mole) in water (1 ml.) and to the resulting solution was added 2,2-diethoxyethylcyanamide (0.34 g., 2 m moles) and the mixture stirred at reflux temperature for 4 hours. Further 2,2-diethoxyethylcyanamide (0.17 g., 1 m mole) was then added and heating with stirring continued for a further 4 hours. The reaction mixture was cooled, the solvent evaporated under reduced pressure and the resulting oily residue dissolved in ethyl acetate (20 ml.) and saturated aqueous NaHCO$_3$ (20 ml.). The aqueous layer was separated, extracted with ethyl acetate and the combined organic layers were dried (MgSO$_4$) and evaporated to dryness. The residual gum was purified by chromatography on silica gel using CH$_2$Cl$_2$/ether/ethanol/acetic acid as eluant in ratios varying from 50:50:15:1 to 10:10:10:1 v/v/v/v to give 103.6 mg. (19%) of diphenylmethyl 7-(imidazol-2-yl)amino-3-(1H-1,2,3-triazol-4-yl)thiomethylceph-3-em-4-carboxylate as a crystalline solid having the following n.m.r. in CDCl$_3$+CD$_3$OD: 3.5 (m, 2H): 3.9 (m, 2H); 5.1 (d, 1H); 5.5 (d, 1H); 6.6 (s, 2H); 6.8 (s, 1H); 7.4 (s, 10H); 7.6 (s, 1H).

A solution of this product in trifluoroacetic acid/anisole 1:1 v/v (0.5 ml.) was stirred at room temperature for 30 minutes. The solvent was evaporated under reduced pressure and the residue was triturated with ether to give 7-(imidazol-2-yl)amino-3-(1H-1,2,3-triazol-4-yl)thiomethylceph-3-em-4-carboxylic acid having the following n.m.r. spectrum in d$_6$DMSO: 2.6 (s, 3H); 3.4 (d, 1H); 3.8 (d, 1H); 4.2 (d, 1H); 4.5 (d, 1H); 5.1 (d, 1H); 5.5 (dd, 1H); 6.9 (s, 2H); 7.9 (s 1H); 9.3 (d, 1H).

EXAMPLE 6

To a suspension of 7-amino-3-(1H-1,2,3-triazol-4-yl)thiomethylceph-3-em-4-carboxylic acid (31.3 g., 0.1 moles) in a mixture of 1,2-dimethyoxyethane (250 ml.) and concentrated HCl (12 ml., 0.138 moles) in water (50 ml.) was added 2,2-diethoxyethylcyanamide (52.05 g., 0.3 moles). The mixture was stirred and heated at 51° C. for 4 hours and the resulting solution was evaporated under reduced pressure to remove the 1,2-dimethoxyethane. The residual oil was diluted with water (250 ml.), the pH of the resulting suspension was adjusted to 4.8 using sodium bicarbonate and then filtered. The filtrate was applied to a column of "Amberlite" XAD-2 (500 ml.) ("Amberlite" is a Trade Mark). The resin was first washed with water (2000 ml.) and then eluted with 40% v/v aqueous methanol. The required fractions were combined and evaporated to dryness to give 7-(imidazol-2-yl)amino-3-(1H-1,2,3-triazol-4-yl)thiomethylceph-3-em-4-carboxylic acid (3.79 g., 10%) having an n.m.r. spectrum identical to the product of Example 5.

EXAMPLE 7

To a suspension of 7-amino-3-(1H-1,2,3-triazol-4-yl)thiomethylceph-3-em-4-carboxylic acid (1.565 g., 0.005 moles) in 1,2-dimethoxyethane (2.5 ml.) and water (17.5 ml.) was added concentrated aqueous hydrochloric acid (0.585 ml., 0.0067 moles) followed by 2,2-dibutoxyethylcyanamide (3.76 g., 0.015 moles). The mixture was stirred and heated for 4 hours at 55° C. under an argon atmosphere. Analysis of the resulting mixture by high performance liquid chromatography on "Hypersil" ODS ("Hypersil" is a Trade Mark) using acetonitrile/methanol/acetic acid/0.1M aqueous phosphoric acid 25:25:25:425 v/v/v/v as eluant revealed the presence of a major component with chromatographic characteristics identical to those of 7-(imidazol-2-yl)amino-3-(1H-1,2,3-triazol-4-yl)thiomethylceph-3-em-4-carboxylic acid.

The process described immediately above was repeated, using equivalent amounts of 2,2-diisobutoxyethylcyanamide and 2,2-dimethoxyethylcyanamide in place of 2,2-dibutoxyethylcyanamide, with identical results.

EXAMPLE 8

The process described in Example 1 was repeated using the appropriate acetals in place of aminoacetaldehyde diethylacetal to give the following compounds having the indicated n.m.r. spectra in $CDCl_3$:

| R | (RO)$_2$—CH—CH$_2$NHCN n.m.r. |
|---|---|
| $C_4H_9$ | 0.9 (m, 6H); 1.5 (m, 8H); 3.17 (d, 2H); 3.5 (m, 5H); 4.6 (t, 1H). |
| $C_4H_9^i$ | 0.96 (d, 12H); 1.86 (m, 2H); 3.16 (d, 2H); 3.3–3.8 (m, 5H); 4.65 (t, 1H). |
| $CH_3$ | 3.12 (s, 6H); 3.2 (d, 2H); 3.5 (br s, 1H); 4.65 (t, 1H). |

EXAMPLE 9

To a solution of t-butyl 7-amino-3-acetoxymethylceph-3-em-4-carboxylate (1.64 g., 5 m moles) and toluene-p-sulphonic acid monohydrate (9.95 g., 5 m moles) in a mixture of water (5 ml.) and acetone (15 ml.) heated under reflux was dropwise added, over 3 hours, a solution of 2,2-dimethoxy-1-methylpropylcyanamide (2.4 g., 15 m moles) in acetone (10 ml.). The mixture was heated under reflux for a further 2 hours, cooled and filtered. The filtrate was evaporated to dryness, the residue taken up in ethyl acetate and the suspension filtered. The filtrate was evaporated to dryness and the residue (4.0 g.) was purified by chromatography on a silica gel column (40 g.) under medium pressure using $CH_2Cl_2$, and then $CH_2Cl_2$ containing progressively increasing amounts of methanol, up to 5% v/v, as eluant. There was thus obtained t-butyl 3-acetoxymethyl-7-(4,5-dimethylimidazol-2-yl) aminoceph-3-em-4-carboxylate toluene-p-sulphonate as a brown powder (0.9 g.; 30%) having the following n.m.r. spectrum in $CDCl_3 + CD_3CO_2D$: 1.5 (s, 9H); 2.1 (s, 3H); 2.2 (s, 6H); 3.4 (d, 2H); 4.75 (d, 1H); 5.1 (d, 1H); 5.15 (d, 1H); 5.7 (d, 1H).

A solution of the above ester (58 mg., 0.1 m mole) in trifluoroacetic acid (1 ml.) was allowed to stand at room temperature for 30 minutes. The solvent was evaporated under reduced pressure and the residue precipitated with ether from a solution in the minimum amount of $CH_2Cl_2$. There was thus obtained 3-acetoxymethyl-7-(4,5-dimethylimidazol-2-yl)aminoceph-3-em-4-carboxylic acid and a mixture of trifluoroacetate and toluene-p-sulphonate salts (42 mg., 84%) having the following n.m.r. spectrum in $d_6DMSO + CD_3COOD$: 2.0 (s, 3H); 3.6 (d, 2H); 4.7 (d, 1H); 5.05 (d, 1H); 5.15 (d, 1H); 5.5 (d, 1H).

The starting material may be obtained as follows:

To a stirred mixture of 3,3-dimethoxybutan-2-one (J.Chem.Soc. 1953, 3135; 1.32 g., 10 m moles) and ammonium acetate (7.7 g., 0.1 mole) in methanol (30 ml.) at 25° C. was added sodium cyanoborohydride (380 mg., 6 m moles) and the pH of the mixture was reduced to 6.0 by addition of a solution of HCl in methanol. The mixture was stirred for 2 hours at 25° C. then the solvent was evaporated under reduced pressure. The residue was taken up in water and the pH adjusted to 5 with 2N aqueous HCl. The solution was washed with ether (3×20 ml.) and the pH of the aqueous phase raised to above 10 by addition of sodium carbonate. The product was extracted with ether (5×20 ml.) and the combined extracts were dried (MgSO$_4$) and evaporated to dryness to give 1-methyl-2,2-dimethoxypropylamine (1.02 g., 77%) as a pale yellow oil having the following n.m.r. spectrum in $CDCl_3$: 1.05 (d, 3H); 1.2 (s, 3H); 1.6 (m, 2H); 3.25 (s, 6H); 3.0–3.6 (m, 1H).

Cyanogen bromide (424 mg., 4 m moles) was added to a solution of 2,2-dimethoxy-1-methylpropylamine (266 mg., 2 m moles) and KHCO$_3$ (400 mg., 4 m moles) in a mixture of water (2 ml.) and methanol (4 ml.). After 15 minutes the mixture was poured into water (150 ml.) and the mixture extracted with $CH_2Cl_2$. The extract was washed with water and brine, dried (MgSO$_4$) and evaporated to dryness to give 2,2-dimethoxy-1-methylpropylcyanamide as a pale yellow oil (280 mg., 88%) having the following n.m.r. spectrum in $CDCl_3$: 1.15 (s, 3H), 1.18 (d, 3H); 3.15 (s, 6H); 3.0–3.6 (m, 1H); 4.0 (m, 1H).

EXAMPLE 10

The process described in Example 6 or 5 may be repeated, using an equivalent amount of the appropriate 3-substituted 7-aminoceph-3-em-4-carboxylic acid, or the diphenylmethyl or t-butyl ester thereof, in place of 7-amino-3-(1H-1,2,3-triazol-4-yl)thiomethylceph-3-em-4-carboxylic acid or the corresponding diphenylmethyl ester respectively, to give the following compounds.

| R | X | Footnotes |
|---|---|---|
| CH₃ | S | 1 |
| CH₂S-(tetrazole-N-CH₂CH₂N(CH₃)₂) | S | 2 |
| CH₂S-(tetrazole-N-CH₃) | S | 3 |
| CH₂S-(thiadiazole-CH₃) | S | 4 |
| CH₂S-(2-COOH-phenyl) | S | 5 |
| CH₂S-(tetrazole-N-CH₂COOH) | S | 6 |
| CH₂S-(thiadiazole) | S | 7 |
| CH₂S-(pyrazolone-CH₂COOH) | S | 8 |
| CH₂S-(tetrazole-N-CH₂SO₃H) | S | 9 |
| CH₂S-(tetrazole-CF₃) | S | 10 |
| CH₂S-(tetrazole-N-CH(CH₃)₂) | S | 11 |
| CH₂S-(tetrazole-N-CH₂CF₃) | S | 12 |
| CH₂S-(tetrazole-N-CH₂CH₂SCH₃) | S | 13 |
| CH₂S-(thiadiazole) | S | 14 |
| CH₂S-(triazinone-N-CH₃ with COOH) | S | 15 |
| CH₂OCH₃ | S | 16 |
| CH₂OCOPh | S | 17 |
| H | S | 18 |
| CH₂S-(thiadiazole-SCH₃) | S | 19 |
| CH₂S-(thiadiazole-SH) | S | 20 |
| CH₂N₃ | S | 21 |
| CH₂NH₂ | S | 22 |
| CH₂NHCOCH₃ | S | 23 |
| Cl | S | 24 |
| CH₂S-(triazole-NH) | S | 25 |
| CH₂S-(triazinone-CH₃ with OH) | S | 26 |
| CH₂S-(thiadiazole-CH₃) | S | 27 |

| | | |
|---|---|---|
| 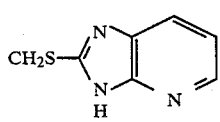 | S | 28 |
| 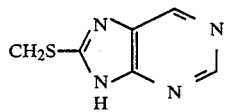 | S | 29 |
| 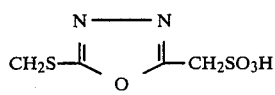 | S | 30 |
| CH₂OH | S | 31 |
| CH₂OCONH₂ | S | 32 |
| 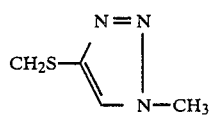 | S | 33 |
| 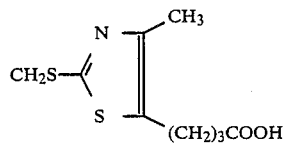 | S | 34 |
| 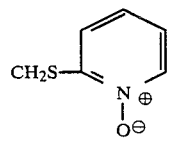 | S | 35 |
| 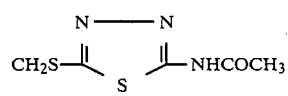 | S | 36 |
| 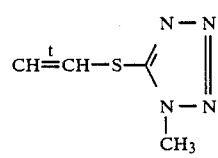 | S | 37 |
| CH₂OCOCH₃ | S—O | 38 |
| Cl | S—O | 39 |
| CH₂OCOCH₃ | S—O | 40 |

Footnotes 1. n.m.r. of TFA salt in d₆DMSO:- 2.075 (s, 3H); 3.48 (q, 2H); 5.13 (d, 1H); 5.5 (q, 1H); 7.07 (s, 2H); 9.45 (d, 1H).
2. n.m.r. in D₂O:- 3.1 (s, 6H); 3.6–4.0 (m, 4H); 4.2 (m, 2H); 4.9 (m, 2H); 5.3–5.5 (2d, 2H); 6.9 (s, 2H).
3. m.p. 120–125° C. and n.m.r. in d₆DMSO:- 3.7 (m, 2H); 3.9 (s, 3H); 4.3 (m, 2H); 5.15 (d, 1H); 5.5 (dd, 1H); 7.0 (s, 2H); 9.4 (d, 1H).
4. m.p. 140–145° C. and n.m.r. in d₆DMSO:- 2.6 (s, 3H); 3.4 (d, 1H); 3.8 (d, 1H); 4.2 (d, 1H); 4.5 (d, 1H); 5.1 (d, 1H); 5.5 (dd, 1H); 6.9 (s, 2H); 9.2 (s, 1H).
5. m.p. 175–180° C. and n.m.r. in d₆DMSO + CD₃COOD:- 3.5 (d, 1H); 3.8 (d, 1H); 4.0 (d, 1H); 4.3 (d, 1H); 5.2 (d, 1H); 5.6 (d, 1H); 7.0 (s, 2H); 7.2–8.0 (m, 3H).
6. n.m.r. in CD₃OD + D₂O:- 3.65 (d, 1H); 3.9 (d, 1H); 4.3 (d, 1H); 4.5 (d, 1H); 5.25 (d, 1H); 5.25 (s, 1H); 5.5 (dd, 1H); 7.0 (s, 2H).
7. n.m.r. in d₆DMSO + CD₃COOD:- 3.52 (d, 1H); 3.79 (d, 1H); 4.33 (d, 1H); 4.6 (d, 1H); 5.12 (d, 1H); 5.58 (d, 1H); 6.83 (s, 2H); 9.49 (s, 1H).
8. n.m.r. of dihydrate in D₂O + TFA:- 3.3 (d, 1H); 3.64 (d, 1H); 3.92 (d, 1H); 4.26 (d, 1H); 4.59 (s, 2H); 4.93 (d, 1H); 5.2 (d, 1H); 6.56 (s, 2H); 6.75 (d, 1H); 7.25 (d, 1H).
9. n.m.r. of toluene-p-sulphonate in d₆DMSO + CD₃COOD:- 2.32 (s, 3H); 3.64 (d, 1H); 3.9 (d, 1H); 4.19 (d, 1H); 4.46 (d, 1H); 5.05 (s, 2H); 5.17 (d, 1H); 5.57 (d, 1H); 7.06 (s, 2H); 7.14 (s, 2H); 7.54 (d, 2H).
10. m.p. 244° C.; n.m.r. in D₂O + TFA:- 3.03 (d, 1H); 3.32 (d, 1H); 3.58 (d, 1H); 3.78 (d, 1H); 4.95 (d, 1H); 6.32 (s, 2H).
11. hydrate, m.p. 219–220° C. (decomp.) and n.m.r. in D₂O + TFA:- 1.5 (d, 6H); 3.6 (d, 1H); 3.83 (d, 1H); 4.2 (s, 2H); 4.6–5.1 (m, 1H); 5.48 (d, 1H); 6.82 (s, 2H).
12. n.m.r. in D₂O + TFA:- 3.35 (d, 1H); 3.6 (d, 1H); 4.14 (s, 2H); 4.98 (d, 1H); 5.0 (q, 2H); 5.26 (d, 1H); 6.64 (s, 2H).
13. n.m.r. in d₆DMSO + CD₃COOD:- 2.05 (s, 3H); 2.97 (t, 2H); 3.52 (d, 1H); 3.78 (d, 1H); 4.36 (bs, 2H); 4.51 (t, 2H); 5.09 (d, 1H); 5.52 (d, 1H); 6.82 (s, 2H).
14. n.m.r. in d₆DMSO + CD₃COOD:- 3.47 (d, 1H); 3.71 (d, 1H); 4.36 (s, 2H); 5.13 (d, 1H); 5.58 (d, 1H); 6.81 (s, 2H); 8.88 (s, 1H).
15. n.m.r. in d₆DMSO:- 3.3 (s, 3H); 3.5 (d, 1H); 3.8 (d, 1H); 3.9 (d, 1H); 4.3 (d, 1H); 5.2 (d, 1H); 5.7 (m, 1H); 6.9 (s, 2H).
16. n.m.r. of TFA salt in d₆DMSO:- 3.2 (s, 3H); 3.5 (m, 2H); 4.2 (s, 2H); 5.2 (d, 1H); 5.5 (d, 1H); 6.9 (d, 2H).
17. n.m.r. of TFA salt in d₆DMSO + CD₃CO₂D:- 3.6 (d, 1H); 3.9 (d, 1H); 5.0 (d, 1H); 5.3 (d, 1H); 5.4 (d, 1H); 5.7 (d, 1H); 7.0 (d, 2H); 7.4–8.1 (m, 5H).
18. n.m.r. of TFA salt in d₆DMSO + CD₃COOD:- 3.65 (s, 2H); 5.1 (d, 1H); 5.7 (d, 1H); 6.55 (t, 1H); 7.0 (s, 2H).
19. n.m.r. of TFA salt in d₆DMSO + CD₃COOD:- 2.8 (s, 3H); 3.7 (d, 1H); 3.8 (d, 1H); 4.3 (d, 1H); 4.5 (d, 1H); 5.2 (d, 1H); 5.6 (d, 1H); 7.0 (s, 2H).
20. n.m.r. of TFA salt in d₆DMSO + CD₃COOD:- 3.5 (d, 1H); 3.6 (d, 1H); 4.1 (d, 1H); 4.2 (d, 1H); 5.05 (d, 1H); 5.6 (d, 1H); 6.8 (s, 2H).
21. n.m.r. of TFA salt containing 20% of the delta-2 isomer in d₆DMSO + CD₃CO₂D:- 3.55 (d, 1H); 3.75 (d, 1H); 4.0 (d, 1H); 4.5 (d, 1H); 5.25 (d, 1H); 5.75 (d, 1H); 7.0 (s, 2H).
22. n.m.r. of ditrifluoroacetate containing 30% of delta-2 isomer in d₆DMSO + CD₃COOD:- 3.2–3.8 (m, 4H); 5.05 (d, 1H); 5.55 (d, 1H); 6.9 (s, 2H).
23. n.m.r. in d₆DMSO + CD₃COOD:- 1.9 (s, 3H); 3.3 (d, 1H); 3.55 (d, 1H); 3.9 (d, 1H); 4.2 (d, 1H); 5.05 (d, 1H); 5.5 (d, 1H); 6.8 (s, 2H); 8.2 (s, 3H).
24. n.m.r. of HCl salt in TFA:- 3.6 (d, 1H); 3.9 (d, 1H); 5.4 (s, 1H); 5.6 (s, 1H); 6.85 (s, 2H).
25. n.m.r. of HCl salt in d₆DMSO:- 3.8 (s, 2H); 4.35 (q, 2H); 5.15 (q, 2H); 7.08 (s, 2H); 9.11 (s, 1H).
26. n.m.r. in d₆DMSO + TFA:- 3.2 (d, 1H); 3.6 (d, 1H); 3.7 (s, 3H); 3.7 (d, 1H); 4.1 (d, 1H); 5.25 (d, 1H); 5.51 (d, 1H); 7.05 (s, 2H).
27. n.m.r. in d₆DMSO + TFA:- 2.65 (s, 3H); 3.45–4.0 (m, 2H); 4.5 (s, 2H); 5.25 (d, 1H); 5.6 (d, 1H); 6.9 (s, 2H).
28. n.m.r. in d₆DMSO:- 3.6 (s, 2H); 3.8–4.1 (m, 2H); 5.05 (d, 1H); 5.45 (d, 1H); 6.8 (s, 2H); 6.8–8.1 (m, 3H).
29. n.m.r. in D₂O + TFA:- 3.95 (d, 1H); 4.22 (d, 1H); 5.0 (br, 2H); 5.52 (d, 1H); 5.8 (d, 1H); 7.2 (s, 2H); 9.0–9.3 (m, 2H).
30. n.m.r. in d₆DMSO/acetic acid:- 3.35–3.85 (m, 2H); 3.65–4.15 (m, 2H); 4.0 (s, 2H); 5.2 (d, 1H); 5.35 (br, 1H); 7.0 (s, 2H).
31. n.m.r. in D₂O + pyridine:- 3.34 (d, 1H); 3.65 (d, 1H); 4.25 (d, 1H); 4.5 (d, 1H); 5.26 (d, 1H); 5.55 (d, 1H); 6.65 (d, 2H).
32. n.m.r. in d₆DMSO + CD₃COOD:- 3.56 (q, 2H); 4.8 (q, 2H); 5.18 (d, 1H); 5.58 (d, 1H); 6.96 (s, 1H).
33. n.m.r. in d₆DMSO + CD₃COOD:- 3.46 (d, 1H); 3.74 (d, 1H); 3.86 (d, 1H); 4.09 (s, 3H); 4.17 (d, 1H); 5.08 (d, 1H); 5.5 (d, 1H); 6.84 (s, 2H); 8.69 (s, 1H).
34. n.m.r. in d₆DMSO + CD₃COOD:- 1.71 (m, 2H);

-continued 2.18 (t, 2H); 2.24 (s, 3H); 2.7 (t, 3H); 3.44 (d, 1H);
3.73 (d, 1H); 4.07 (d, 1H); 4.47 (d, 1H); 5.06 (d, 1H);
5.54 (d, 1H); 6.8 (s, 2H).

35. n.m.r. in d$_6$DMSO + CD$_3$COOD:- 3.46 (d, 1H);
3.73 (d, 1H); 4.17 (s, 2H); 5.16 (d, 1H); 5.55 (d, 1H);
6.8 (s, 2H); 8.28 (dd, 1H); 7.05–7.69 (3H).

36. n.m.r. in d$_6$DMSO + CD$_3$COOD:- 2.13 (s, 3H);
3.41 (d, 1H); 3.73 (d, 1H); 4.19 (d, 1H); 4.44 (d, 1H);
5.06 (d, 1H); 5.54 (d, 1H); 6.71 (s, 2H).

37. n.m.r. in d$_6$DMSO + CD$_3$COOD:- 3.62 (m, 2H);
3.9 (s, 3H); 5.1 (d, 1H); 5.5 (d, 1H); 6.7 (d, 1H); 7.2 (d, 1H); 6.75 (s, 2H).

38. S—O in β configuration; n.m.r. of trifluoroacetate salt in CD$_3$COOD:- 2.0 (s, 3H); 3.44 (d, 1H);
3.97 (d, 1H); 4.65 (d, 1H); 4.95 (d, 1H); 5.23 (d, 1H);
5.8 (d, 1H); 6.87 (s, 2H).

39. mixture of α and β isomers at the 1-position;
n.m.r. in d$_6$DMSO + TFA:- 4.0 (s, 1H); 4.15 (s, 1H);
4.95 and 5.1 (d, 1H); 5.7 and 5.8 (d, 1H); 7.05 (s, 2H).

40. S—O in α configuration; n.m.r. of toluene-p-sulphonate salt in d$_6$DMSO + CD$_3$COOD:- 2.05 (s, 3H);
2.28 (s, 3H); 3.75 (m, 2H); 4.65 (d, 1H); 5.05 (d, 1H);
5.05 (d, 1H); 5.7 (d, 1H); 7.08 (s, 2H); 7.3 (q, 4H).

I claim:

1. A process for the manufacture of a cephalosporin derivative of the Formula I:

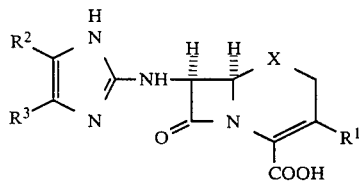

in which

X is sulphur, oxygen or sulphinyl;

$R^1$ is hydrogen, chlorine, methyl, acetoxymethyl, methoxymethyl, hydroxymethyl, azidomethyl, aminomethyl, benzoyloxy methyl, acetylaminomethyl, carbamoyloxymethyl, 2-(1-methyltetrazol-5-ylthio)-trans-vinyl, 1-methyl-1H-tetrazol-5-ylthiomethyl, 1-carboxymethyl-1H-tetrazol-5-ylthiomethyl, 1-(2-dimethylamino)ethyl-1H-tetrazol 5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-d]pyrimidin-2-ylthiomethyl; and $R^2$ and $R^3$ are hydrogen;

which comprises reacting a compound of the formula XXXIII:

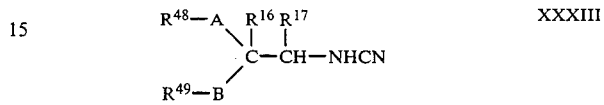

in which $R^{16}$ and $R^{17}$ are hydrogen, A and B are oxygen and $R^{48}$ and $R^{49}$ are joined to form an ethylene or propylene chain which is optionally substituted by one or two 1–6C alkyl radicals or $R^{48}$ and $R^{49,}$ which may be the same or different, are 1–6C alkyl or 1–6C alkanoyl radicals, or $R^{48}$ and $R^{49}$ are joined to form a 1,3,5-trioxane ring which is substituted on the remaining two carbon atoms by radicals of the formula XXXIV:

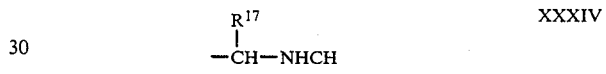

with a compound of the Formuls $X^1$:

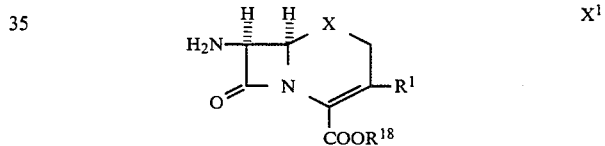

in which X and $R^1$ have the meanings stated above and $R^{18}$ is hydrogen, t-butyl, diphenylmethyl, benzyl, p-nitrobenzyl, p-methoxybenzyl or 2,2,2-trichloroethyl.

2. A process as claimed in claim 1 which is carried out in a diluent or solvent in the presence of acid at a pH in the range of 1 to 4 and at a temperature between 20° C. and the boiling point of the diluent or solvent.

3. A process as claimed in claim 1 in which, when $R^{18}$ is t-butyl or diphenyl methyl, it is replaced by hydrogen by treatment with formic or trifluoroacetic acid, when $R^{18}$ is benzyl, p-nitrobenzyl or p-methoxybenzyl it is replaced by hydrogen by hydrogenolysis, and when $R^{18}$ is 2,2,2-trichloroethyl it is replaced by hydrogen with zinc/acetic acid.

4. A process as claimed in claim 1 in which about three molecular equivalents of the reactant of the formula XXXIII thereof, are used.

5. A process as claimed in claim 1 in which $R^1$ is 1H-1,2,3-triazol-4-ylthiomethyl.

* * * * *

UNITED STATES PATENT AND TRADEMARK OFFICE
CERTIFICATE OF CORRECTION

PATENT NO. : 4,497,949

DATED : February 5, 1985

INVENTOR(S) : Frank LOFTUS

It is certified that error appears in the above-identified patent and that said Letters Patent is hereby corrected as shown below:

On the title page add:

--[30]    Foreign Application Priority Data

June 19, 1981 [GB] United Kingdom....1889481--.

Signed and Sealed this

Ninth Day of July 1985

[SEAL]

Attest:

DONALD J. QUIGG

*Attesting Officer*    *Acting Commissioner of Patents and Trademarks*